United States Patent [19]

Brizard

[11] Patent Number: 5,492,675
[45] Date of Patent: Feb. 20, 1996

[54] DEODORANT SYSTEM

[76] Inventor: Cyril J. C. Brizard, 20026 Pacific Coast Hwy., Malibu, Calif. 90265

[21] Appl. No.: 300,454

[22] Filed: Sep. 2, 1994

[51] Int. Cl.$^6$ ................................................ A62B 7/08
[52] U.S. Cl. .................... 422/122; 206/461; 206/464; 206/524.4; 422/119; 422/120
[58] Field of Search ....................... 422/120, 122, 422/123, 311, 306, 4, 5, 119; 239/35, 57, 60, 55; 424/76.1, 76.21; 206/461, 464, 524.4, 0.7, 204, 213.1, DIG. 806

[56] References Cited

U.S. PATENT DOCUMENTS

| | | | |
|---|---|---|---|
| 1,757,530 | 5/1930 | Keim | 206/0.5 X |
| 1,806,149 | 5/1931 | Daugherty | 206/0.5 X |
| 2,201,524 | 5/1940 | Esty | 206/459.1 X |
| 2,233,614 | 3/1941 | Krotoschiner | 356/215 |
| 2,247,600 | 7/1941 | Brennan et al. | 239/57 |
| 2,251,058 | 7/1941 | Kirkman | 422/5 X |
| 2,613,991 | 10/1952 | Schindler | 206/0.5 X |
| 2,765,046 | 10/1956 | Rondholz | 422/4 X |
| 3,138,432 | 6/1964 | Kleinhans | 422/122 |
| 3,424,380 | 1/1969 | Curran | 239/60 |
| 3,844,478 | 10/1974 | Davis | 23.9/57 |
| 4,014,432 | 3/1977 | Clothier et al. | 206/0.5 |
| 4,081,501 | 3/1978 | Mather | 264/89 |
| 4,155,500 | 5/1979 | Dutcher | 239/5.9 X |
| 4,208,012 | 6/1980 | Dutcher | 239/57 |
| 4,283,011 | 8/1981 | Spector | 239/57 X |
| 4,624,366 | 11/1986 | Marder et al. | 206/620 |
| 4,752,087 | 6/1988 | Weisbach | 206/459.1 X |
| 4,817,998 | 4/1989 | Ryder et al. | 422/300 X |
| 4,905,898 | 3/1990 | Wade | 239/55 X |
| 4,921,636 | 5/1990 | Traas | 239/60 X |
| 4,995,556 | 2/1991 | Arnold, III | 422/120 |
| 5,164,178 | 11/1992 | Muysson | 239/60 X |
| 5,186,903 | 2/1993 | Cornwall | 422/122 |

*Primary Examiner*—Robert J. Warden
*Assistant Examiner*—Krisanne M. Thornton
*Attorney, Agent, or Firm*—Kelly, Bauersfeld & Lowry

[57] ABSTRACT

A deodorant system includes a compact container for an odor absorbent, which may be temporarily secured to another surface such as an interior wall of a refrigerator or a garbage container, and which includes a calendar to assist in determining a replacement date for the deodorant system. A plastic housing is attached to a front face of a cardboard base plate to provide a container for the powdered odor absorbent. Several apertures are provided through a wall of the housing opposite the base plate, and an adhesive label is adhered over substantially the entire front face of the housing wall. Removal of the adhesive label exposes the odor absorbent, which consists primarily of calcium carbonate and activated carbon. Either a suction cup or an adhesive strip may be fixed to a rear face of the base plate for purposes of temporarily securing the packaging to another surface.

19 Claims, 2 Drawing Sheets

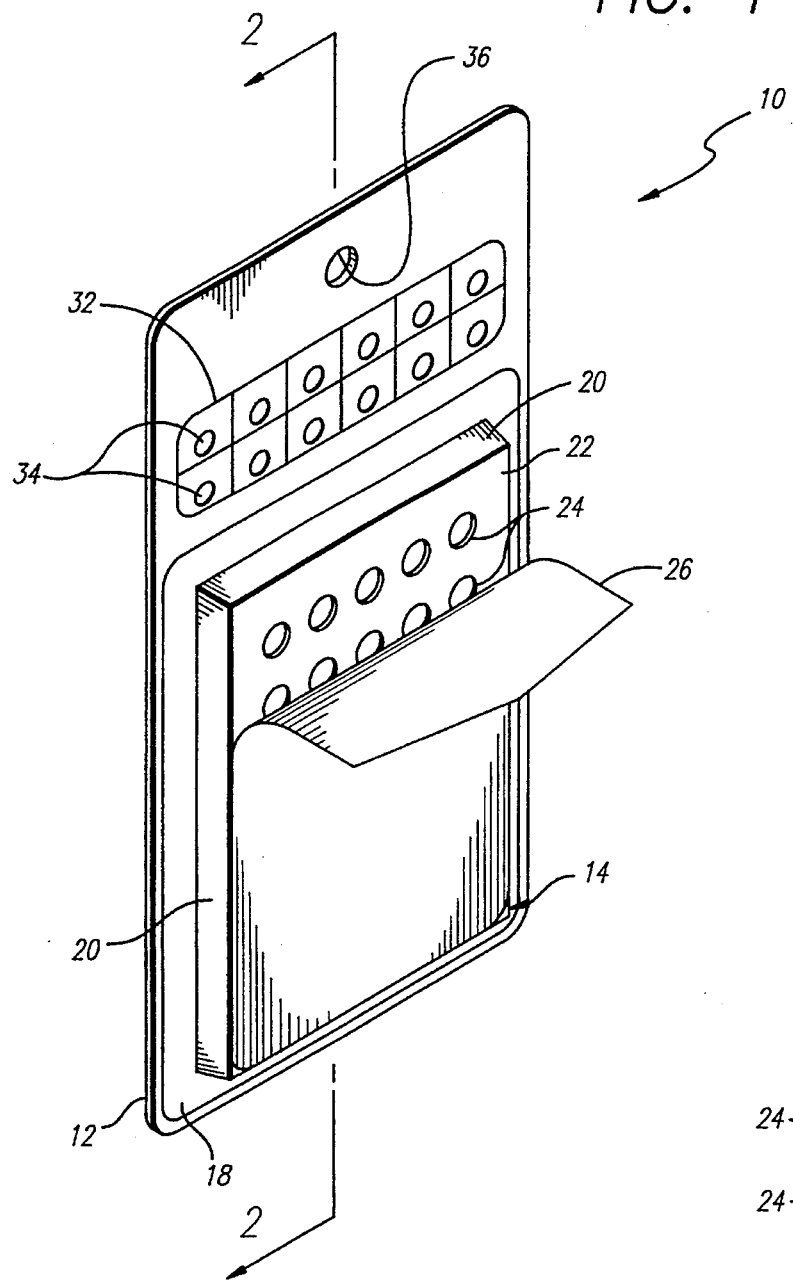
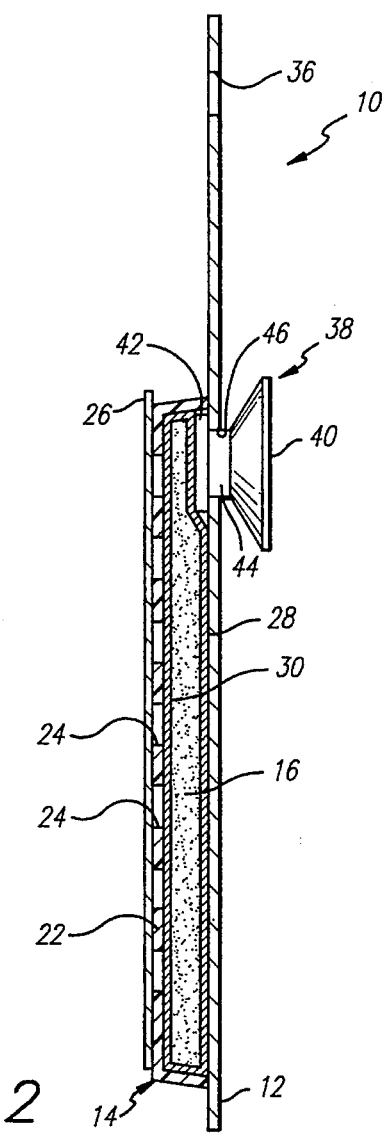
FIG. 1
FIG. 2

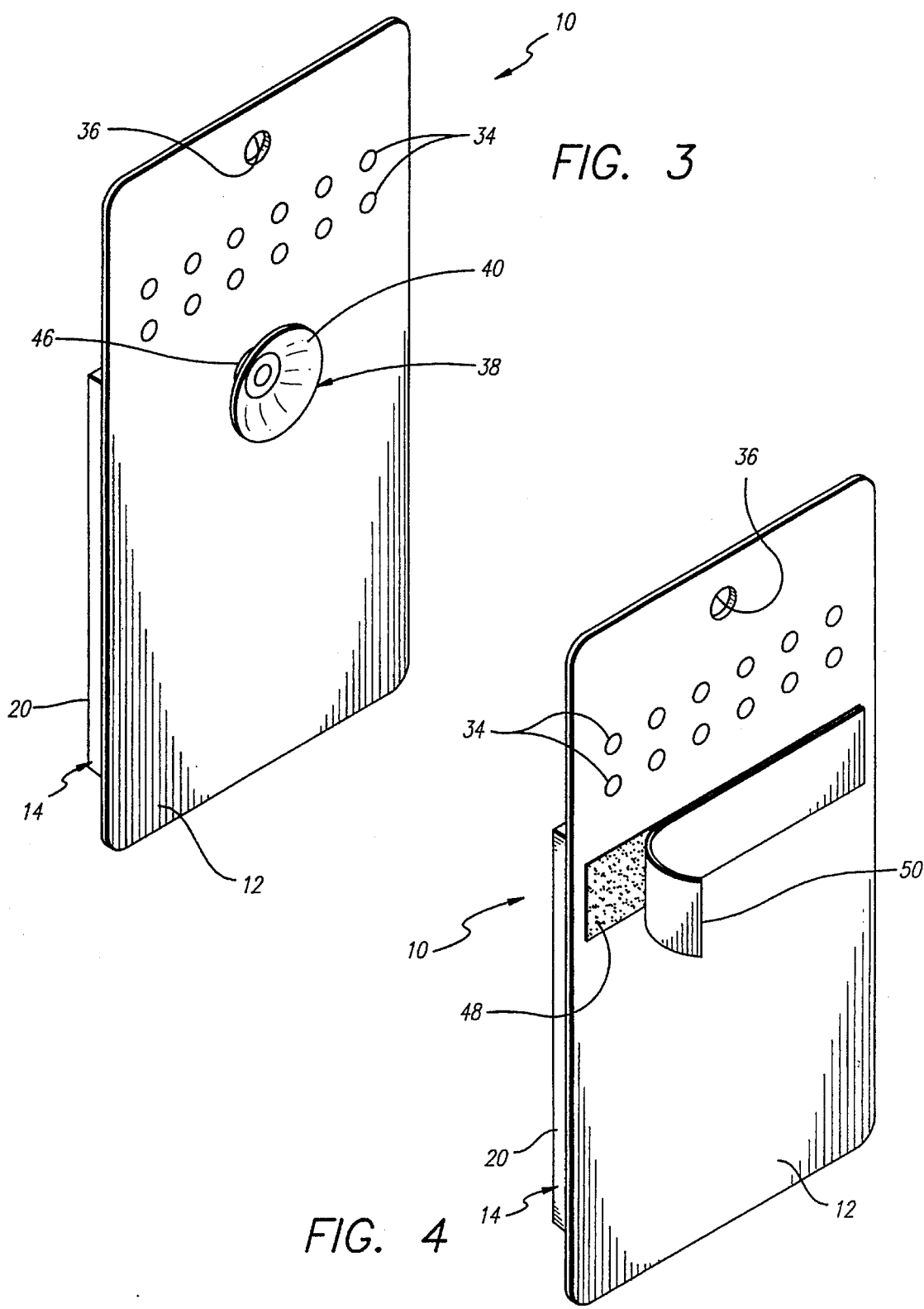

DEODORANT SYSTEM

BACKGROUND OF THE INVENTION

This invention relates generally to deodorant systems. More particularly, the present invention relates to a disposable deodorant system wherein a powdered odor absorbent is packaged within a unique container that may be adhered to a wall within a confined space and which provides a reference calendar for determining when the deodorant system is to be discarded and replaced.

Room deodorizers employing either a wick of material saturated with deodorant or a wax block having deodorant therein, for steadily releasing vapors into an area to either mask or neutralize objectionable odors in a confined space are well known and commercially available. Such solid air fresheners are often sold in sealed outer containers having one or more openings in the container walls to permit room air to circulate past the air freshener material or the air freshener material to defuse through the openings and mingle with the room air to freshen the same. The openings are frequently covered by a panel of release paper until a consumer is ready to use the air freshener material. The panel is then stripped away to expose the openings and thus the surface of the solid air freshener within the container to room air.

Alternatively, containers or carton s containing certain powdered material have been used to remove or eliminate objectionable odors. For example, it is a common practice to place boxes of materials such as sodium bicarbonate (baking soda) in refrigerators, closets and the like, to absorb undesired odors from food, clothing, etc. One disadvantage of the boxes is that only the top portion of the box opens and only a limited surface area of powdered material is exposed. Another disadvantage is that in the event that such a box is upset, the contents may be distributed in a wholly undesired manner.

Most deodorants work either as a perfume to mask odors, or as a physical deodorant to absorb odors. Less common biological deodorants work by deadening a person's sense of smell. In certain confined areas, such as within a refrigerator or a garbage receptacle, odor absorbents and neutralizers are preferred.

Although the use of an odor absorbent material within a confined space is not new, packages utilized to hold the odor absorbent material have traditionally been less than ideal. As mentioned above, placement of an open box of baking soda within a refrigerator only exposes the upper level of the baking soda within the box to atmosphere. Thus, most of the baking soda goes unused. Further, the baking soda itself does not have an unlimited useful life. Once the upper layer of the exposed baking soda has been exposed for an extended period of time, it loses its effectiveness and, usually, the entire box is thrown out. Further, such boxes and other free standing containers for deodorants cannot be used in certain environments where shelf space is limited or unavailable.

Accordingly, there has been a need for a novel deodorant system which overcomes the above-noted drawbacks, and which can be manufactured in an economical fashion. Such a novel deodorant system should include packaging which may be temporarily secured to a vertical wall, and provide means for indicating a replacement date for the deodorant system without the use of a writing instrument. Additionally, a deodorant system is needed which absorbs odors significantly better than baking soda. The present invention fulfills these needs and provides other related advantages.

SUMMARY OF THE INVENTION

The present invention resides in an improved deodorant system which is compact, easy to manufacture, and may be used in a wide variety of confined space environments to absorb many different types of odors. The deodorant system comprises a planar base and a housing attached to a front face of the base. The housing includes at least one aperture through a wall thereof opposite the base. Removable means are adhered to a front face of the housing wall, for sealing the at least one aperture until removed from the housing wall to expose a deodorant within the housing to atmosphere.

In a preferred form of the invention, a plastic housing is attached to a front face of a cardboard base plate. The housing is preferably provided with a plurality of similarly sized apertures through a wall of the housing opposite the base plate. An adhesive label is adhered over substantially the entire front face of the housing wall for sealing the apertures and thus enclosing an internal container area defined by the base plate and the housing.

The deodorant comprises a powdered or granular material capable of absorbing odors in a confined area. The deodorant consists essentially of calcium carbonate ($CaCO_3$) in an amount of 50% to 60% by weight, activated carbon in an amount of 35% to 45% by weight, stearic acid in an amount of 2% to 4% by weight, and urea in an amount of 1% to 3% by weight. The deodorant is placed within a bag which, in turn, is placed within the internal container area defined by the base plate and the housing. A portion of the bag provides a porous liner disposed between the deodorant and the apertures.

Means associated with the base are provided for indicating a replacement date for the deodorant system. The indicating means includes a calendar printed onto the base, and removable portions of the base associated with the calendar. These removable portions are die cut dots that may be punched out from the base plate.

Means are also provided for temporarily securing the base to another surface. In one embodiment, the securing means includes a rearwardly extending suction cup fixed to the base. In another embodiment the securing means includes an adhesive strip fixed to the rear face of the base plate.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 1 is a front perspective view of a deodorant system embodying the invention, wherein an adhesive label is shown partially peeled away from the front face of a housing wall;

FIG. 2 is an enlarged sectional view taken generally along the line 2—2 of FIG. 1;

FIG. 3 is a rear elevational perspective view of the deodorant system shown in FIGS. 1 and 2, illustrating the use of a suction cup fixed to a base plate and extending rearwardly therefrom, for temporarily securing the base plate to another surface; and FIG. 4 is a rear perspective view similar to FIG. 3 of a deodorant system utilizing an alternative means for temporarily securing the base to another surface, which comprises an adhesive strip fixed to a rear face of the base plate.

DETAILED DESCRIPTION OF THE PREFERRED EMBODIMENTS

As shown in the drawings for purposes of illustration, the present invention is concerned with a novel deodorant system, generally designated by the reference number 10. In accordance with the present invention, the deodorant system 10 comprises a generally rectangular planar cardboard base plate 12, a plastic housing 14 attached to a front face of the base plate 12, and a deodorant 16 contained between the base plate and the housing.

The housing 14 includes a lower rectangular flange 18 that lies flat against a corresponding portion of the front face of the base plate 12, and is adhered thereto by a suitable adhesive. Four side walls 20 extend outwardly away from the base plate 12 to a front housing wall 22 which lies in a plane parallel to the plane of the base plate 12. The front housing wall 22 is provided a plurality of apertures 24 therethrough, and an adhesive label 26 is adhered over substantially the entire front face of the housing wall 22 so as to cover and seal the apertures 24.

The base plate 12, the housing 14 and the adhesive label 26 form an air-tight container in which the deodorant 16 is stored prior to use. To expose the deodorant 16 to atmosphere, the adhesive label 26 is simply peeled away from the housing wall 22 so as to uncover the apertures 24 (see FIG. 1).

With reference to FIG. 2, the deodorant 16 comprises a powdered or granular material capable of absorbing odors in a confined area. The deodorant consists essentially of calcium carbonate ($CaCO_3$) in an amount of 50% to 60% by weight, activated carbon in an amount of 35% to 45% by weight, stearic acid in an amount of 2% to 4% by weight, and urea in an amount of 1% to 3% by weight. Most preferably, the deodorant 16 consists of calcium carbonate ($CaCO_3$) in an amount of 55% by weight, activated carbon in an amount of 40% by weight, stearic acid in an amount of 3% by weight, and urea in an amount of 2% by weight. The deodorant 16 is contained within a bag 28 which is placed between the housing 14 and the base plate 12. At least the portion of the bag 28 underlying the apertures 24 comprises a porous liner 30 through which air may freely pass to the deodorant 16, but which prevents the powdered deodorant from leaving its confined space within the housing 14 through the apertures 24.

Above the housing 14, the base plate 12 is provided with means for indicating a replacement date for the deodorant system 10. The indicating means includes a calendar 32 printed onto the base plate 12, and die cut removable dots 34 associated with each month of the calendar 32. In use, once the adhesive label 26 has been peeled away from the housing wall 22 to expose the deodorant 16 to atmosphere through the apertures 24, the dot 34 representing the replacement month is punched from the base plate 12 to provide an easy reminder of when the deodorant system 10 should be replaced. Instructions for replacing the deodorant system 10 may be conveniently printed on the rear face of the base plate 12 or on the front of the adhesive label 26.

Above the calendar 32, an aperture 36 may be provided through the base plate 12 for hanging the deodorant system 10 on a nail or the like by the consumer, or on a point of purchase display in a retail store.

The deodorant system 10 also includes means for temporarily securing the base plate 12 to another surface, such as an interior wall of a refrigerator or garbage container. In one embodiment, shown in FIGS. 2 and 3, the securing means includes a suction cup assembly 38. The suction cup assembly 38 includes a rearwardly facing suction cup 40, a forwardly facing head 42, and an intermediate neck 44. An aperture 46 is provided through the base plate 12 through which the head 42 and neck 44 are inserted. The assembly 38 is preferably an integral molded unit so that the head 42 and the neck 44 have the same material characteristics as the suction cup 40. Thus, the head 42 deforms as it is passed through the aperture 46, and resiliently regains it original configuration once adjacent the front face of the base plate 12 in order to prevent withdrawal of the suction cup assembly 38 through the aperture 46.

In an alternative form of the invention illustrated in FIG. 4, the suction cup assembly 38 is replaced with an adhesive strip 48 fixed to the rear face of the base plate 12 below the dots 34. A peel-off paper backing 50 is placed over the adhesive strip 48, and is removed prior to pressing the adhesive strip 48 against a suitable support surface for positioning the deodorant system 10 in a desired location.

From the foregoing it is to be appreciated that the deodorant system 10 of the present invention is quite easy to use in confined spaces, and may be adapted to provide the most desirable means for temporarily securing the base plate 12 to another surface. The calendar 32 advantageously permits a user to indicate when the deodorant system 10 should be replaced, without requiring the use of a writing instrument. Further, the deodorant system 10 may be manufactured in an economical fashion. Moreover, the powdered deodorant has been shown to absorb odors 100% better than baking soda. In this regard, laboratory tests show that the deodorant 16 absorbed all odors tested at least twice as effectively as baking soda when the two products were tested on an equal weight basis.

Although two particular embodiments of the invention have been described in detail for purposes of illustration, various modifications of each may be made without departing from the spirit and scope of the invention. For example, regarding the calendar, other alternatives which do not require the use of a writing instrument can be used, such as a color changing indicator which would turn red (for example) when the deodorant is saturated. Accordingly, the invention is not to be limited, except as by the appended claims.

I claim:

1. A deodorant system, comprising:

a planar base;

a housing attached to a front face of the base, the housing including at least one aperture through a wall thereof opposite the base;

a deodorant within the housing capable of absorbing odors in a confined area, the deodorant consisting essentially of calcium carbonate ($CaCO_3$) in an amount of 50% to 60% by weight, activated carbon in an amount of 35% to 45% by weight, stearic acid in an amount of 2% to 4% by weight, and urea in an amount of 1% to 3% by weight; and removable means adhered to a front face of the housing wall, for sealing the at least one aperture until removed from the housing wall to expose the deodorant within the housing to atmosphere.

2. The deodorant system of claim 1, wherein the removable sealing means includes an adhesive label adhered over substantially the entire front face of the housing wall.

3. The deodorant system of claim 1, including means for temporarily securing the base to another surface.

4. The deodorant system of claim 3, wherein the securing means includes a suction cup fixed to the base and extending rearwardly therefrom.

5. The deodorant system of claim 3, wherein the securing means includes an adhesive strip fixed to a rear face of the base.

6. The deodorant system of claim 1, wherein the base includes means for indicating a replacement date for the deodorant system.

7. The deodorant system of claim 6, wherein the indicating means includes indicia removable from the base.

8. The deodorant system of claim 7, wherein the indicating means includes a calendar printed onto the base.

9. The deodorant system of claim 1, including a porous liner disposed between the deodorant and the at least one aperture.

10. The deodorant system of claim 9, wherein the deodorant comprises a powdered or granular material, and wherein the porous liner comprises a portion of a bag for containing the powdered material.

11. A deodorant system, comprising:

a cardboard base plate;

a plastic housing attached to a front face of the base plate, the housing including at least one aperture through a wall thereof opposite the base plate;

a deodorant within the housing consisting essentially of calcium carbonate ($CaCO_3$) in an amount of 50% to 60% by weight, activated carbon in an amount of 35% to 45% by weight, stearic acid in an amount of 2% to 4% by weight, and urea in an amount of 1% to 3% by weight;

removable means adhered to a front face of the housing wall, for sealing the at least one aperture until removed from the housing wall to expose the deodorant within the housing to atmosphere;

means for temporarily securing the base plate to another surface; and means on the base plate, for indicating a replacement date for the deodorant system.

12. The deodorant system of claim 11, wherein the removable sealing means includes an adhesive label adhered over substantially the entire front face of the housing wall.

13. The deodorant system of claim 11, wherein the securing means includes a suction cup fixed to the base plate and extending rearwardly therefrom.

14. The deodorant system of claim 11, wherein the securing means includes an adhesive strip fixed to a rear face of the base plate.

15. The deodorant system of claim 11, wherein the indicating means includes a calendar printed onto the base plate, and wherein the calendar includes removable portions of the base plate.

16. The deodorant system of claim 11, including a porous liner disposed between the deodorant and the at least one aperture.

17. A deodorant system, comprising:

a base plate;

a housing attached to a front face of the base plate, the housing including at least one aperture through a wall thereof opposite the base plate;

a deodorant comprising a powdered or granular material capable of absorbing odors in a confined area, the deodorant consisting essentially of calcium carbonate ($CaCO_3$) in an amount of 50% to 60% by weight, activated carbon in an amount of 35% to 45% by weight, stearic acid in an amount of 2% to 4% by weight, and urea in an amount of 1% to 3% by weight;

removable means adhered to a front face of the housing wall, for sealing the at least one aperture until removed from the housing wall to expose the deodorant within the housing to atmosphere, the removable sealing means including an adhesive label adhered over substantially the entire front face of the housing wall;

means for temporarily securing the base plate to another surface;

means for indicating a replacement date for the deodorant system, the indicating means including a calendar printed onto the base plate, wherein the calendar includes removable portions of the base plate; and a porous liner disposed between the deodorant and the at least one aperture, the porous liner comprising a portion of a bag for containing the deodorant.

18. The deodorant system of claim 17, wherein the securing means includes a suction cup fixed to the base plate and extending rearwardly therefrom.

19. The deodorant system of claim 17, wherein the securing means includes an adhesive strip fixed to a rear face of the base plate.

* * * * *